United States Patent

Taylor et al.

[11] Patent Number: 5,917,086
[45] Date of Patent: Jun. 29, 1999

[54] PURIFICATION PROCESS

[75] Inventors: James Philip Taylor, Macclesfield; John Barry Henshall, Urmston; John Whitworth, Audenshaw, all of United Kingdom

[73] Assignee: Ciba Specialty Chemicals Corporation, Tarrytown, N.Y.

[21] Appl. No.: 09/005,156

[22] Filed: Jan. 9, 1998

[30] Foreign Application Priority Data

Jan. 9, 1997 [GB] United Kingdom ................ 9700375.0

[51] Int. Cl.⁶ ...................... C07C 229/52; C07D 295/00; C07D 211/34; C07D 207/04
[52] U.S. Cl. ........................... 562/441; 544/172; 546/239; 548/572
[58] Field of Search ............................ 562/441; 544/172; 546/239; 548/572

[56] References Cited

U.S. PATENT DOCUMENTS 5,371,285  12/1994  Kondo et al. ......................... 562/441

OTHER PUBLICATIONS

Encyclopedia of Separation Technology, vol. 1, Douglas M. Ruthven, ed., John Wiley & Sons, 1997, pp. 814–815.
Chem. Abst. 121:35021.
Derwent Abstract 75–00537W.

*Primary Examiner*—Brian M. Burn
*Assistant Examiner*—Brian J. Davis
*Attorney, Agent, or Firm*—Kevin T. Mansfield

[57] ABSTRACT

A method for the purification of a keto acid having the general formula

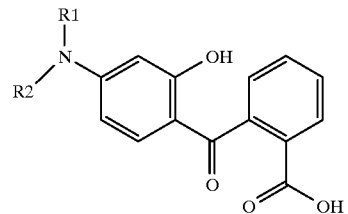

wherein R1 and R2 independently represent a straight or branched chain alkyl of 1–18 carbon atoms, a cycloalkyl of 4–8 carbon atoms or a phenyl both of which may be substituted by at least one substituent selected from the group consisting of halogen atoms and alkyls having 1–4 carbon atoms, an aralkyl of 7–10 carbon atoms, alkoxyalkyl having 2–20 carbon atoms, tetrahydrofuryl alkyl, alkylcarboxy alkyl, alkyl carboxy benzyl, or R1 and R2 together with the adjacent nitrogen atom may form a heterocyclic ring, or one of $R_1$ and $R_2$ is hydrogen, which comprises slurrying the keto acid with an alcohol solvent, maintaining the slurry at elevated temperature in a sealed vessel until the Rhodamine impurity has dissolved, cooling and isolating the pure keto acid by filtration.

6 Claims, No Drawings

PURIFICATION PROCESS

FIELD OF INVENTION

The invention relates to a method of purifying keto acids. Such keto acids are useful intermediates for the production of fluoran compounds used as dyestuff in pressure or heat-sensitive recording.

PRIOR ART

The keto acids have previously been produced by the reaction of N, N-dialkylaminophenol with phthalic anhydride in a molar ratio of 0.5–2.0. The synthesis has been performed in tiie absence of solvent or in the presence of an inactive solvent such as toluene, xylene or tetrahydrofuran, at a temperature of 80–150° C., as a solution or slurry dependant on the nature of the N, N-dialkyl amino phenol. Solvent has been used in a ratio of 0.5–4.5 w/w with respect to N, N-dialkylaminophenol. The synthesis also provides a significant amount of highly coloured rhodamine dyes by the reaction of keto acid with N,N-dialkylaminophenol, thereby causing a problem in making pure keto acids.

To solve the above problem, there has been proposed a method in which an aqueous solution of sodium hydroxide is added to the resultant reaction mixture, the reaction mixture is heated to decompose by-produced rhodamines to alkali metal salts of the keto acid, the alkali metal salt of the keto acid is crystallised and then redissolved in water, and then the salt is neutralised in water to recover the keto acid, as disclosed in Japanese patent laid open No. 62-70350. However, the method needs a large number of steps and, in addition, the method produces a large amount of neutralization waste water. Another solution to the problem has proposed purification of the keto acid by crystallisation from solution at elevated temperatures and pressures, as disclosed in EP 511,019. However, dissolution of the keto acid requires high temperatures and a pressure of several atmospheric pressures.

SUMMARY OF INVENTION

It is therefore, an object of this invention to provide a method of purifying crude keto acids without the generation of large amounts of aqueous waste and without recourse to the specialist equipment needed for dissolving the keto acid.

The invention provides an improved method for the purification of a keto acid having the general formula

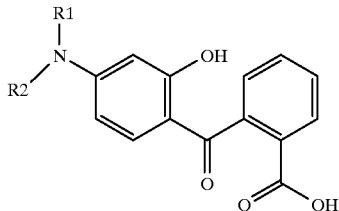

wherein R1 and R2 independently represent a straight or branched chain alkyl of 1–18 carbon atoms, a cycloalkyl of 4–8 carbon atoms or a phenyl both of which may be substituted by at least one substituent selected from the group consisting of halogen atoms and alkyls having 1–4 carbon atoms, an aralkyl of 7–10 carbon atoms, alkoxyalkyl having 2–20 carbon atoms, tetrahydrofuryl alkyl, alkylcarboxy alkyl, alkyl carboxy benzyl, or R1 and R2 together with the adjacent nitrogen atom may form a heterocyclic ring, or one of $R_1$ and $R_2$ is hydrogen, which comprises slurrying the keto acid with an alcohol solvent, maintaining the slurry at elevated temperature in a sealed vessel until the Rhodamine impurity has dissolved, cooling and isolating the pure keto acid by filtration.

This gives the following advantages:
1. Purification without the generation of large volumes of aqueous waste.
2. Purification without recourse to high pressure reactions and the consequent high degree of danger and high cost of facility.

DETAILED DESCRIPTION OF THE INVENTION

The keto acids which may be purified by the process of the invention include, but are not limited to:

2-hydroxy-4-N,N-di-n-propyl amino-2'-carboxybenzophenone, 2-hydroxy-4-N,N-di-n-butyl amino-2'-carboxybenzophenone, 2-hydroxy-4-N,N-di-n-pentyl amino-2'-carboxybenzophenone, 2-hydroxy-4-N,N-di-n-hexyl amino-2'-carboxybenzophenone, 2-hydroxy-4-N,N-diisopropyl amino-2'-carboxybenzophenone, 2-hydroxy-4-N,N-disecbutyl amino-2'-carboxybenzophenone, 2-hydroxy-4-N,N-diisobutyl amino-2'-carboxybenzophenone, 2-hydroxy-4-N,N-diisoamyl amino-2'-carboxybenzophenone, 2-hydroxy-4-N,methyl-N-cyclohexyl amino-2'-carboxybenzophenone, 2-hydroxy-4-N,methyl-N-phenyl amino-2'-carboxybenzophenone, 2-hydroxy-4-N,methyl-N-(2-methylphenyl) amino-2'-carboxybenzophenone, 2-hydroxy-4-N-methyl-N-(3-methylphenyl) amino-2'-carboxybenzophenone, 2-hydroxy-4-N-methyl-N-(4-methylphenyl) amino-2'-carboxybenzophenone, 2-hydroxy-4-N-methyl-N-propyl amino-2'-carboxybenzophenone, 2-hydroxy-4-N-methyl-N-isopropyl amino-2'-carboxybenzophenone, 2-hydroxy-4-N-methyl-N-butyl amino-2'-carboxybenzophenone, 2-hydroxy-4-N-methyl-N-isobutyl amino-2'-carboxybenzophenone, 2-hydroxy-4-N-methyl-N-secbutyl amino-2'-carboxybenzophenone, 2-hydroxy-4-N-methyl-N-pentyl amino-2'-carboxybenzophenone, 2-hydroxy-4-N-methyl-N-1-methylbutyl amino-2'-carboxybenzophenone, 2-hydroxy-4-N-methyl-N-isoamyl amino-2'-carboxybenzophenone, 2-hydroxy-4-N-methyl-N-1-methylpentyl amino-2'-carboxybenzophenone, 2-hydroxy-4-N-methyl-N-hexyl amino-2'-carboxybenzophenone, 2-hydroxy-4-N-methyl-N-tetrahydrofurylmethyl amino-2'-carboxybenzophenone, 2-hydroxy-4-N-methyl-N-ethoxypropyl amino-2'-carboxybenzophenone,
2-hydroxy-4-N-methyl-N-cyclohexylmethyl amino-2'-carboxybenzophenone,
2-hydroxy-4-N-methyl-N-phenethyl amino-2'-carboxybenzophenone,
2-hydroxy-4-N-ethyl-N-cyclohexyl amino-2'-carboxybenzophenone,
2-hydroxy-4-N-ethyl-N-phenyl amino-2'-carboxybenzophenone,
2-hydroxy-4-N-ethyl-N-(2-methylphenyl) amino-2'-carboxybenzophenone,
2-hydroxy-4-N-ethyl-N-(3-methylphenyl) amino-2'-carboxybenzophenone,
2-hydroxy-4-N-ethyl-N-(4-methylphenyl) amino-2'-carboxybenzophenone,
2-hydroxy-4-N-ethyl-N-propyi amino-2'-carboxybenzophenone,
2-hydroxy-4-N-ethyl-N-isopropyl amino-2'-carboxybenzophenone,
2-hydroxy-4-N-ethyl-N-butyl amino-2'-carboxybenzophenone,
2-hydroxy-4-N-ethyl-N-isobutyl amino-2'-carboxybenzophenone,
2-hydroxy-4-N-ethyl-N-secbutyl amino-2'-carboxybenzophenone,
2-hydroxy-4-N-ethyl-N-pentyl amino-2'-carboxybenzophenone,
2-hydroxy-4-N-ethyl-N-1-methylbutyl amino-2'-carboxybenzophenone,
2-hydroxy-4-N-ethyl-N-isoamyl amino-2'-carboxybenzophenone,
2-hydroxy-4-N-ethyl-N-1-methylpentyl amino-2'-carboxybenzophenone,
2-hydroxy-4-N-ethyl-N-hexyl amino-2'-carboxybenzophenone,
2-hydroxy-4-N-ethyl-N-tetrahydrofurylmethyl amino-2'-carboxybenzophenone,
2-hydroxy-4-N-ethyl-N-ethoxypropyl amino-2'-carboxybenzophenone,
2-hydroxy-4-N-ethyl-N-cyclohexyl methyl amino-2'-carboxybenzophenone,
2-hydroxy-4-N-ethyl-N-phenethyl amino-2'-carboxybenzophenone,
2-hydroxy-4-N-propyl-N-cyclohexyl amino-2'-carboxybenzophenone,
2-hydroxy-4-N-propyl-N-phenyl amino-2'-carboxybenzophenone,
2-hydroxy-4-N-propyl-N-(2-methylphenyl) amino-2'-carboxybenzophenone,
2-hydroxy-4-N-propyl-N-(3-methylphenyl) amino-2'-carboxybenzophenone,
2-hydroxy-4-N-propyl-N-(4-methylphenyl) amino-2'-carboxybenzophenone,
2-hydroxy-4-N-propyl-N-isopropyl amino-2'-carboxybenzophenone,
2-hydroxy-4-N-propyl-N-butyl amino-2'-carboxybenzophenone,
2-hydroxy-4-N-propyl-N-isobutyl amino-2'-carboxybenzophenone,
2-hydroxy-4-N-propyl-N-secbutyl amino-2'-carboxybenzophenone,
2-hydroxy-4-N-propyl-N-pentyl amino-2'-carboxybenzophenone,
2-hydroxy-4-N-propyl-N-1-methylbutyl amino-2'-carboxybenzophenone,
2-hydroxy-4-N-propyl-N-isoamyl amino-2'-carboxybenzophenone,
2-hydroxy-4-N-propyl-N-1-methylpentyl amino-2'-carboxybenzophenone,
2-hydroxy-4-N-propyl-N-hexyl amino-2'-carboxybenzophenone,
2-hydroxy-4-N-propyl-N-tetrahydrofurylmethyl amino-2'-carboxybenzophenone,
2-hydroxy-4-N-propyl-N-ethoxypropyl amino-2'-carboxybenzophenone,
2-hydroxy-4-N-propyl-N-cyclohexyl methyl amino-2'-carboxybenzophenone,
2-hydroxy-4-N-propyl-N-phenethyl amino-2'-carboxybenzophenone,
2-hydroxy-4-N-butyl-N-cyclohexyl amino-2'-carboxybenzophenone,
2-hydroxy-4-N-butyl-N-phenyl amino-2'-carboxybenzophenone,
2-hydroxy-4-N-butyl-N-(2-methylphenyl) amino-2'-carboxybenzophenone,
2-hydroxy-4-N-butyl-N-(3-methylphenyl) amino-2'-carboxybenzophenone,
2-hydroxy-4-N-butyl-N-(4-methylphenyl) amino-2'-carboxybenzophenone,
2-hydroxy-4-N-butyl-N-propyl amino-2'-carboxybenzophenone,
2-hydroxy-4-N-butyl-N-isopropyl amino-2'-carboxybenzophenone,
2-hydroxy-4-N-butyl-N-isobutyl amino-2'-carboxybenzophenone,
2-hydroxy-4-N-butyl-N-secbutyl amino-2'-carboxybenzophenone,
2-hydroxy-4-N-butyl-N-pentyl amino-2'-carboxybenzophenone,
2-hydroxy-4-N-butyl-N-1-methylbutyl amino-2'-carboxybenzophenone,
2-hydroxy-4-N-butyl-N-isoamyl amino-2'-carboxybenzophenone,
2-hydroxy-4-N-butyl-N-1-methylpentyl amino-2'-carboxybenzophenone,
2-hydroxy-4-N-butyl-N-hexyl amino-2'-carboxybenzophenone,
2-hydroxy-4-N-butyl-N-tetrahydrofurylmethyl amino-2'-carboxybenzophenone,
2-hydroxy-4-N-butyl-N-ethoxypropyl amino-2'-carboxybenzophenone,
2-hydroxy-4-N-butyl-N-cyclohexylmethyl amino-2'-carboxybenzophenone,
2-hydroxy-4-N-butyl-N-phenethyl amino-2'-carboxybenzophenone,
2-hydroxy-4-N-phenyl amino-2'-carboxybenzophenone
2-hydroxy-4-N-(2-methylphenyl) amino-2'-carboxybenzophenone
2-hydroxy-4-N-(3-methylphenyl) amino-2'-carboxybenzophenone
2-hydroxy-4-N-(4-methylphenyl) amino-2'-carboxybenzophenone 2-hydroxy-4-N-cyclohexyl amino-2'-carboxybenzophenone 2-hydroxy-4-N-pyrrolidinyl -2'-carboxybenzophenone 2-hydroxy-4-N-(2-methylpyrrolidinyl) -2'-carboxybenzophenone 2-hydroxy-4-N-(3-methylpyrrolidinyl) -2'-carboxybenzophenone.

2-hydroxy-4-N-morpholinyl -2'-carboxybenzophenone.

2-hydroxy-4-N-piperidinyl -2'-carboxybenzophenone 2-hydroxy-4-N-(2-methylpiperidinyl) -2'-carboxybenzophenone 2-hydroxy-4-N-(3-methylpiperidinyl) -2'-carboxybenzophenone.

2-hydroxy-4-N-(4-methylpiperidinyl) -2'-carboxybenzophenone.

For the purification of the keto acid as above mentioned, the keto acid is slurried with a solvent. The ratio of solvent to keto acid may be from 0.1 to 5.0, preferably 0.4–0.9. The slurry is maintained at elevated temperature in a sealed vessel. This generates a slight pressure, usually of 1–2 bar. The temperature may be up to the boiling point of the solvent. The time needed to dissolve the Rhodamine impurity may vary depending on the actual compounds present. Usually a time of about 1 hour is sufficient, but times of up to 20 hours may be used if necessary.

The pressure, temperature and solvent ratio are determined so that the keto acid remains as a slurry throughout the reaction. The slurry is then cooled e.g. to 20° C., and isolated by filtration. The resulting material contains little or none of the rhodamine impurity.

There may be used as the solvent, alcohols, for example, methanol, ethanol, propanols such as isopropanols, butanols such as n-butanol or pentanol. There may also be used a mixture of the alcohol with water or a mixture of the alcohol with a hydrocarbon solvent, preferably an aromatic hydrocarbon of 6–10 carbon atoms such as toluene or xylene, or an aliphatic hydrocarbon of 5–10 carbon atoms such as pentane, hexane or heptane.

By the way of an example, the purification of, 2-hydroxy-4-N,N-di-n-butylamino-2'-carboxy benzophenone may be carried out in an alcohol, such as methanol, the preferred amount of solvent being in the range 0.4–0.9 by weight with respect to the keto acid.

The invention is illustrated by the following Examples.

EXAMPLE 1

An amount of 200 g of 2-hydroxy-4-N, N-di-n-butylamino-2'-carboxy benzophenone and 158 g of methanol is charged to a 1 litre reaction vessel equipped with a pressure gauge. The vessel is sealed and the reaction mixture is heated to 84–86° C. and stirred. The pressure within the vessel is observed and does not exceed 2.0 bar. The keto acid remains as a slurry throughout the purification.

After 1 hour the slurry is cooled to room temperature and the keto acid isolated by filtration. The filtercake is washed with methanol (3×40 g) and dried to give 186 g of high purity keto acid. The rhodamine impurity is reduced from 0.47% to 0.045% as determined by UV absorbance.

EXAMPLE 2

An amount of 150 g of 2-hydroxy-4-N, N-diethylamino-2'-carboxy benzophenone and 118.5 g of methanol is charged to a 1 litre reaction vessel equipped with a pressure gauge. The vessel is sealed and the reaction mixture is heated to 84–86° C. and stirred. The pressure within the vessel is observed and does not exceed 2.0 bar. The keto acid remains as a slurry throughout the purification.

After 1 hour the slurry is cooled to room temperature. The keto acid is isolated by filtration and dried to give 146.8 g of high purity keto acid. The rhodamine impurity is reduced from 0.1% to 0.03% as determined by UV absorbance.

We claim:

1. A method for the purification of a keto acid having the formula

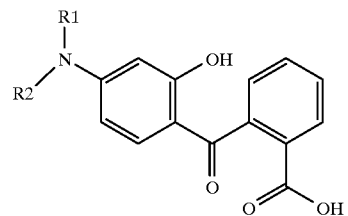

wherein R1 and R2 independently represent a straight or branched chain alkyl of 1–18 carbon atoms, a cycloalkyl of 4–8 carbon atoms or a phenyl, each of which may be substituted by at least one substituent selected from the group consisting of halogen atoms and alkyls having 1–4 carbon atoms, an aralkyl of 7–10 carbon atoms, alkoxyalkyl having 2–20 carbon atoms, tetrahydrofuryl alkyl, alkylcarboxy alkyl, alkyl carboxy benzyl, or R1 and R2 together with the adjacent nitrogen atom may form a pyrrolidino, morpholino or piperidino ring, or one of $R_1$ and $R_2$ is hydrogen, which comprises slurrying the keto acid with 0.1 to 5.0 parts by weight of an alcohol solvent, maintaining the slurry at elevated temperature in a sealed vessel until the Rhodamine impurity has dissolved, cooling and isolating the pure keto acid by filtration.

2. The method of claim 1 in which the ratio of solvent to keto acid is from 0.4 to 0.9.

3. The method of claim 1 claim in which the temperature is up to the boiling point of the solvent.

4. The method of claim 1 in which the solvent is an alcohol, a mixture of alcohol and water, or a mixture of alcohol with a hydrocarbon solvent.

5. The method of claim 1 in which the alcohol is methanol, ethanol, isopropanol, n-butanol, or pentanol.

6. The method of claim 1 in which the keto acid is 2-hydroxy-4-N, N-di-n-butylamino-2'-carboxy benzophenone or 2-hydroxy-4-N, N-diethylamino-2'-carboxy benzophenone.

* * * * *